United States Patent [19]

Stipp et al.

[11] Patent Number: 5,741,538
[45] Date of Patent: Apr. 21, 1998

[54] LOW DENSITY SOLUBLE COFFEE PRODUCTS HAVING INCREASED PARTICLE STRENGTH AND RAPID HOT WATER SOLUBILITY

[75] Inventors: Gordon Keith Stipp; Robert Lee White, both of Cincinnati, Ohio

[73] Assignee: The Procter & Gamble Company, Cincinnati, Ohio

[21] Appl. No.: 605,603

[22] Filed: Feb. 22, 1996

[51] Int. Cl.$^6$ .................................................. A23F 5/00
[52] U.S. Cl. ........................................... 426/594; 426/650
[58] Field of Search ................................... 426/594, 650

[56] References Cited

U.S. PATENT DOCUMENTS

| | | | |
|---|---|---|---|
| 2,360,342 | 10/1944 | Heyman | 99/71 |
| 2,750,998 | 6/1956 | Moore | 159/4 |
| 2,809,895 | 10/1957 | Swisher | 99/140 |
| 2,906,630 | 9/1959 | Turkot et al. | 99/206 |
| 2,929,716 | 3/1960 | Barch et al. | 99/71 |
| 2,929,717 | 3/1960 | Eskew | 99/71 |
| 3,419,399 | 12/1968 | Earle, Jr. et al. | 99/71 |
| 3,436,227 | 4/1969 | Bergeron et al. | 99/71 |
| 3,493,388 | 2/1970 | Hair | 99/71 |
| 3,583,075 | 6/1971 | Folsom | 34/5 |
| 3,615,669 | 10/1971 | Hair et al. | 99/71 |
| 3,620,756 | 11/1971 | Strobel et al. | 99/71 |
| 3,637,397 | 1/1972 | Menzies et al. | 99/65 |
| 3,650,769 | 3/1972 | Fritzberg | 99/134 |
| 3,652,293 | 3/1972 | Lombana et al. | 99/71 |
| 3,717,472 | 2/1973 | Strobel | 99/65 |
| 3,997,685 | 12/1976 | Strobel | 426/594 |
| 4,100,305 | 7/1978 | Gregg | 426/385 |
| 4,154,864 | 5/1979 | Risler et al. | 426/594 |
| 4,313,265 | 2/1982 | Dwyer, Jr. | 34/5 |
| 4,610,890 | 9/1986 | Miller et al. | 426/651 |
| 4,820,534 | 4/1989 | Saleeb et al. | 426/96 |
| 4,820,543 | 4/1989 | Osawa | 426/650 |
| 4,904,484 | 2/1990 | Small et al. | 426/45 |
| 4,919,962 | 4/1990 | Arora et al. | 426/594 |
| 5,035,908 | 7/1991 | Arora et al. | 426/388 |
| 5,079,026 | 1/1992 | Arora et al. | 426/594 |
| 5,087,461 | 2/1992 | Levine et al. | 426/96 |
| 5,120,559 | 6/1992 | Rizvi et al. | 426/446 |
| 5,171,595 | 12/1992 | Hsu et al. | 426/329 |
| 5,236,729 | 8/1993 | Schlecht et al. | 426/417 |
| 5,399,368 | 3/1995 | Garwood et al. | 426/307 |
| 5,417,992 | 5/1995 | Rizvi et al. | 426/283 |
| 5,474,792 | 12/1995 | Arora et al. | 426/594 |

FOREIGN PATENT DOCUMENTS

| | | | |
|---|---|---|---|
| 823142 | 9/1969 | Canada | 99/76 |
| 94/10852 | 5/1994 | WIPO . | |

OTHER PUBLICATIONS

Micromeritics; PoreSizer 9320; Operator's Manual; Part No. 932–42801–01; Sep. 1, 1989.

Lowell et al.; Interpretation of mercury porosimetry data; *Power Surface Area and Porosity*; 1979; pp. 87–96, 97–120, 205–216, 217–224.

AccuPyc 1330 Pycnometer; Operator's Manual V2.01; Part No. 133–42801–01; Sep. 25, 1992.

Jenike et al.; Compressibility Tester; Operating Instructions; *Storage and Flow of Solids*; Dec. 1981; pp. 1–5.

Birks; Power quality assurance by compaction analysis; *Manufacturing Chemist*; Apr. 1990; pp. 22–26.

*Primary Examiner*—Anthony J. Weier
*Attorney, Agent, or Firm*—Eric W. Guttag; Rose Ann Dabek

[57] ABSTRACT

Soluble coffee products having a chunkier physical appearance more like that of granular roast and ground coffee products, lower apparent (bulk) densities compared to prior agglomerated spray dried instant coffee products and better solubility than prior freeze dried instant coffee products when added directly to hot water. These soluble coffee products are made by forming a relatively thin glassy coffee strip or sheet from a thermoplastic melt of soluble coffee solids, water, coffee aroma and flavor volatiles and optionally solubility enhancing components and then gradually applying vacuum conditions to this glassy strip or sheet over several cycles while heated to a pliable and deformable state such that the strip/sheet expands in a controlled manner from about 2 to about 10 times its initial thickness to provide a porous open-celled coffee matrix where the pores have a median pore size typically in the range of from about 3 to about 25 microns. This porous coffee matrix is then dried and granulated to provide a soluble coffee product that can be easily measured out by consumers to provide differing brew strengths and can be used across a range of consumer preparation practices.

11 Claims, No Drawings

LOW DENSITY SOLUBLE COFFEE PRODUCTS HAVING INCREASED PARTICLE STRENGTH AND RAPID HOT WATER SOLUBILITY

TECHNICAL FIELD

The present application relates to soluble coffee products having a relatively low apparent (bulk) density, increased particle strength, and rapid solubility in hot water that can be easily measured out and used across a range of consumer preparation practices. The present application further relates to a process for making these coffee products that retains more coffee aroma and flavor volatiles and is economical to carry out.

BACKGROUND OF THE INVENTION

Current instant coffee products are primarily manufactured as spray dried powders. These spray dried powders are typically made by spraying concentrated coffee extract as an atomized fine mist into a spray drying tower many stories high. The air flow within the tower is hot enough to evaporate the residual moisture in the extract so that the falling coffee solids become a dry powder, usually light brown in color, by the time they reach the bottom of the tower. Before spray drying, this concentrated coffee extract is often combined with aroma and flavor volatiles (typically referred to as "stripper condensate") that is removed ("stripped") from the coffee extract before it is concentrated.

Spray drying is a relatively economical way to make instant coffee. However, both the appearance and solubility of these spray dried powders fall short of what is desired by most coffee consumers. These spray dried powders are relatively free in particle size (e.g., from about 0.1 to about 0.3 mm in diameter) and thus do not look like roast and ground coffee granules. These spray dried powders also tend to dissolve poorly when added directly to hot water. The added powder floats on top of the water, foams, and can form an unsightly ring on the inside of the cup.

Spray drying has the additional adverse effect of driving off important coffee aroma and flavor volatiles. Typically, only about 50 to about 60% of the stripped aroma and flavor volatiles that are combined with concentrated coffee extract are retained after spray drying. This loss of aroma and flavor volatiles detracts from the hue coffee flavor of the product. In commercial practice, this volatile loss is compensated for by adding aromatized (coffee) oil to the spray dried coffee powder. Unfortunately, this aromatized oil can cause the spray dried particles to clump together into a less flowable mass that is more difficult to spoon out as a measured quantity of instant coffee.

To improve the appearance and hot water solubility of spray dried coffee powders, these powders are usually agglomerated. Agglomeration is typically carried out by spraying steam onto the spray dried powder. This steam partially melts the spray dried powder so that the particles coalesce and cluster together into larger structures (e.g., about 3 mm in size). These larger agglomerated structures improve the appearance, flowability and solubility of the instant coffee product. Even so, agglomerated spray dried coffee still suffers from the aroma and flavor volatile loss caused by the initial spray drying process. Also, agglomerated spray dried coffee particles are relatively fragile and tend to break up into finer particles in the jar during in-plant handling and during shipment to the trade. The tendency of agglomerates to break-up into finer particles leads to problems in consistently measuring a spoonful of product from the jar. This can make it difficult for the consumer to prepare a cup of coffee having the desired brew strength.

Freeze drying is an alternative commercial process for drying soluble coffee products. Freeze-dried instant coffee is prepared by freezing a coffee extract prepared in a manner the same or similar to that of the extract used in spray drying. This frozen extract, with or without granulation, is placed in a chamber held under a vacuum (e.g., less than 500 micron Hg absolute pressure) and maintained at relatively low temperatures (e.g., less than −15° F. (−26° C.)). The frozen extract is then gently heated to cause sublimation of the ice crystals from the extract, thus removing the water. Because water is removed gently and carefully without significant heating of the frozen extract, freeze dried instant coffees can achieve a high degree of aroma and flavor volatile retention.

Freeze dried instant coffee products can be granulated to provide a chunky physical appearance that is more like that of roast and ground coffee. The sublimation of ice crystals that occurs during freeze drying creates an extremely porous coffee structure. As a result, freeze dried coffee products typically have a lower density than spray dried and especially agglomerated instant coffee products. Freeze dried products typically have poorer solubility than agglomerated spray dried products, especially when added to a cup of hot water. The freeze dried chunks tend to float on the surface and can result in a messy cup preparation. Freeze dried coffee also tends to be lighter in color than spray dried/ agglomerated instant coffee products and thus different in color from granular roast and ground coffee. Freeze drying processes are also more capital intensive and costly to run than spray drying/agglomeration processes. This means freeze dried instant coffee products are generally more expensive than spray dried/agglomerated instant coffee products.

In the United States, instant coffee products are typically consumed at about a 1% median coffee solid concentration. However, a significant portion of these consumers prefer a milder cup of coffee made at a lower concentration. Unfortunately, these consumers find it difficult to measure out current spray dried/agglomerated instant coffee products to achieve their desired flavor strength. The presence of frees in current spray dried/agglomerated products makes dosage control difficult and requires measuring out partial spoonfuls of product. This is both inconvenient and confusing to the consumer. The most practical way of delivering such a milder cup of coffee for these consumers is to reduce the bulk density such that a lower mount of coffee solids is dosed in each spoonful of product.

In addition, about half of the consumers of soluble coffee products prepare their drinkable beverage using a microwave. Typically, the water is first heated and then the desired dosage of product is added directly on top of the heated water. As noted above, freeze dried products do not dissolve very well when prepared in such fashion. This means the consumer must either accept a messy cup appearance or change their preparation habits.

To summarize, conventional coffee processing technology cannot readily meet the consumer need to deliver a lower and consistent spoon dosage that is readily soluble under all expected methods of consumer preparation. Although it is possible to make a low density spray dried/agglomerated soluble coffee product, such products have a tendency to break-up readily into undesirable fine particles. This makes spoon dosage control even more difficult for those consumers preferring a milder cup of coffee. Further, the manufacture of low density freeze dried products is difficult, expensive, and leads to poor solubility under certain preparation conditions, (e.g., when the coffee is added directly on top of hot water). There thus exists a significant consumer need to develop low density soluble coffee products that have less particle breakup, and exhibit better hot water solubility across a range of preparation practices.

DISCLOSURE OF THE INVENTION

The present invention relates to soluble coffee products having a particle size in the range of from about 6 mesh (3360 microns) to about 40 mesh (420 microns). These soluble coffee products comprise:

a. a soluble amorphous porous open-celled coffee matrix having:
  (1) a bulk density of from about 0.10 to about 0.35 g/cc;
  (2) a particle density of from about 1.0 to about 1.35 g/cc;
  (3) a porosity of from about 15 to about 40%;
  (4) a median pore size of from about 1 to about 30 microns;
  (5) a sink time of about 45 seconds or less;
  (6) a compressive strength index of about 5 or less;
  (7) a moisture content of about 7% or less;
  (8) optionally, but preferably, solubility enhancing components; and
b. coffee aroma and flavor volaries encapsulated within the soluble coffee matrix.

The present invention further relates to a process for making these soluble coffee products. This process comprises the steps of:

a. forming a thermoplastic melt from a mixture comprising from about 85 to about 97% soluble coffee solids, from about 3 to about 15% water, coffee aroma and flavor volatiles and optionally, but preferably, solubility enhancing components;
b. forming the thermoplastic melt into a solidified elongated coffee structure having a thickness of from about 1/16 to about 1/2 inches and encapsulating the coffee aroma and flavor volatiles within the structure;
c. expanding in a controlled manner the solidified coffee structure while in a pliable and deformable state such that the structure expands from about 2 to about 10 times its initial thickness to provide a porous opencelled coffee matrix where the pores have a median pore size of from about 1 to about 30 microns;
d. drying the porous coffee matrix to a moisture content of about 7% or less; and
e. granulating the dried matrix to a particle size of from about 6 mesh (3360 microns) to about 40 mesh (420 microns).

The soluble coffee products of the present invention have increased compressire strength compared to conventional spray dried and agglomerated instant coffee products. As a result, these soluble coffee products have relatively lower particle break up compared to conventional agglomerated coffee products. This increased compressive strength is surprisingly achieved even though these soluble coffee products have relatively low apparent (bulk) densities (i.e., from about 0.10 to about 0.35 g/cc). The process of the present invention for making these coffee products also allows far greater retention of desired coffee aroma and flavor volatiles (e.g., from about 75 to about 95% retention of such volatiles), especially compared to prior processes for spraying drying instant coffee. These coffee products also have better solubility in hot water compared to current freeze dried coffee products, particularly when added directly to the water.

The soluble coffee products of the present invention typically have a chunkier physical appearance more like that of granular roast and ground coffee products, especially compared to conventional spray dried and agglomerated instant coffee products. The soluble coffee products according to the present invention also deliver a lower mount of product in each spoonful. Unlike conventional freeze dried instant coffee products, the soluble coffee products of the present invention exhibit good solubility, even when the soluble products are directly added to the hot water already in the cup. Also, the soluble coffee products of the present invention can be made to have darker colors than freeze dried instant coffee products and more like roast and ground coffee granules without losing other desired characteristics. The process for making soluble coffee products according to the present invention can achieve aroma and flavor volatile retention rates comparable to conventional freeze drying instant coffee processes without the high capital investment and operational costs associated with freeze drying.

The soluble coffee products of the present invention are relatively easy to spoon out to provide a measured quantity of product. This allows those consumers desiring differing brew strengths (e.g., milder cups of coffee) to control the dosage more easily to achieve the result they desire. Indeed, the soluble coffee products of the present invention can be used across a range of consumer preparation practices. This allows many instant coffee consumers the flexibility to prepare their drinkable beverage without having to alter how they like to prepare their beverage.

DETAILED DESCRIPTION

A. Definitions

As used herein, the terms "instant coffee" and "soluble coffee" are used interchangeably to refer to coffee products that are relatively soluble in water, especially hot water.

As used herein, the term "particle density" refers to the specific gravity of the coffee particles measured by a gas displacement technique in a He Pycnometer, as described in Operator's Manual V2.01 "AccuPyc 1330 Pycnometer" (Sep. 25, 1992).

As used herein, the term "porosity" refers to a measure of the void space in solid coffee particles determined by Hg pore symmetry. See pages 205–224 of Lowell and Shields, POWDER SURFACE AREA AND POROSITY, (Chapman and Hall 1984)

As used herein, the term "median pore size" refers to the median of the pore size calculated on a volume distribution basis by Hg pore symmetry, as described in Micromeritics Operator's Manual for "PoreSizer 9320" (Sep. 1, 1989) and pages 98–120 of Lowell and Shields, POWDER SURFACE AREA AND POROSITY, (Chapman and Hall 1984)

As used herein, the term "compressive strength index" refers to the value that is 100 times the Flow Factor measured on an Andrew Jenkins Flow Tester, as described in Jenike & Johanson's manual entitled "Compressiblity Tester Operating Instructions" (Revised December 1981) and pages 22–26 of Birks, "Powder Quality Assurance by Compaction Analysis," *Manufacturing Chemist,* (April 1990).

As used herein, the term "sink time" refers to the time necessary for 2 grams of soluble coffee to wet and penetrate (i.e., sink below) the surface of 180 ml of nominal 170°–180° F. (77°–82° C.) hot water in an eight ounce cup.

As used herein, the terms "bulk density" and "apparent density" refer interchangeably to untamped bulk density values. Bulk and apparent densities referred to herein can be measured by conventional methods for determining untamped bulk densities. See pp. 130–131 of Sivetz & Foote, COFFEE PROCESSING TECHNOLOGY, Vol. II (Avi Publishing Company 1963).

As used herein, coffee color refers to the L, a, and b readings measured on a Hunter colorimeter. See pages 985–95 of R. S. Hunter, "Photoelectric Color Difference Meter," *J. of the Optical Soc. of Amer.*, Volume 48, (1958).

The terms "moisture" and "water" are used interchangeably herein.

All particle sizes referred to herein are based on the U.S. Standard Sieve Screen Series. See page 701 of Sivetz & Desrosier, COFFEE TECHNOLOGY (Avi Publishing Co. 1979).

As used herein, the term "comprising" means various components and processing steps can be conjointly employed in the soluble coffee products and process of the present invention. Accordingly, the term "comprising" encompasses the more restrictive terms "consisting essentially of" and "consisting of."

All amounts, parts, ratios and percentages used herein are by weight unless otherwise specified.

B. Sources of Soluble Coffee Solids, Aroma and Flavor Volatiles and Other Optional Components Soluble coffee solids used in the present invention can be obtained from, or can be prepared by, any convenient process for making instant coffee products. A variety of such processes are known to those skilled in the art. Typically, instant coffee is prepared by roasting and grinding a blend of coffee beans, extracting the roast and ground coffee with water to form an aqueous coffee extract, and drying the extract to form instant coffee. Coffee solids useful in the present invention are typically obtained by conventional spray drying processes and preferably using concentrated coffee extract that has not been combined with stripper condensate or other sources of coffee aroma and flavor volatiles. Representative spray drying processes that can provide suitable coffee solids are disclosed in, for example, pages 382–513 of Sivetz & Foote, COFFEE PROCESSING TECHNOLOGY, Vol. I (Avi Publishing Co. 1963); U.S. Pat. No. 2,771,343 (Chase et al), issued Nov. 20, 1956; U.S. Pat. No. 2,750,998 (Moore), issued Jun. 19, 1956; and U.S. Pat. No. 2,469,553 (Hall), issued May 10, 1949, all of which are incorporated by reference. Other suitable processes for providing soluble coffee solids for use in the present invention are disclosed in, for example, U.S. Pat. No. 3,436,227 (Bergeron et al)., issued Apr. 1, 1969; U.S. Pat. No. 3,493,388 (Hair), issued Feb. 3, 1970; U.S. Pat. No. 3,615,669 (Hair et at), issued Oct. 26, 1971; U.S. Pat. No. 3,620,756, (Strobel et at), issued November 16, 1971; U.S. Pat. No. 3,652,293 (Lombann et at), issued Mar. 28, 1972, all of which are incorporated by reference. If desired, the coffee solids can be obtained by simply concentrating the coffee extract from an instant coffee process to the desired solids content. The source of coffee solids can also be formed by combining dried powders and extracts of various concentrations.

Coffee aroma and flavor volatiles suitable for use in the present invention can be derived from a variety of sources. For example, coffee aroma and flavor volatiles can be obtained from gases evolved during roasting, grinding and/or flaking of roast and ground and/or flaked coffee products, as well as the respective condensed aroma frosts. Typically, these coffee aroma and flavor volatiles are obtained from instant coffee processes, including stripper condensate removed from coffee extract prior to evaporative concentration, stripped coffee oil, coffee aroma and flavor volatiles desorbed from roast and ground coffee according to the processes described in, for example, U.S. Pat. No. 3,717,472 (Strobel), issued Feb. 20, 1973; U.S. Pat. No. 3,997,685 (Strobel) issued Dec. 14, 1976; and U.S. Pat. No. 4,100,305 (Gregg), issued Jul. 11, 1978, all of which are incorporated by reference, and the like. These coffee aroma and flavor volatiles can be further concentrated or fractionated by a variety of methods well known to those skilled in the art.

These soluble coffee products can be optionally, but preferably, formulated to contain solubility enhancing components. As used herein, the term "solubility enhancing components" refer to those materials that enhance the ability of the soluble coffee solids to rapidly dissolve in water, especially hot water. Representative examples of suitable solubility enhancing components for use in the present invention include coffee oil, coffee oil derived fatty acids, the respective water soluble salts of such acids and/or the respective mono- and/or di-glycerides of coffee oil, coffee oil that has been lipase treated or hydrolyzed to increase the level of coffee off derived fatty acids and/or their respective salts, monoglycerides and diglycerides, coffee materials that inherently contain coffee off and/or the respective fatty acids, fatty acid salts and/or mono- and diglycerides of coffee off, other food grade fatty acids and/or their respective salts, other food grade emulsifiers such as mono- and di-glycerides that are capable of enhancing the ability of soluble coffee to dissolve in water, especially hot water, as well as mixtures of any of these components. It has been found that the inclusion of these solubility enhancing components can greatly reduce (as measured by "sink time" and visual cup appearance) how long it takes to dissolve a measured quantity of the soluble coffee products of the present invention in water, especially hot water.

Other optional components typically used with instant coffee can also be used in the soluble coffee products of the present invention. These other components include noncoffee flavorants and flavor extracts such as vanilla, chocolate, chocolate mint, cocoa, chocolate liquors, almond nut, amaretto, anisette, apple, brandy, cappuccino, chamomile, cherry, cinnamon, cinnamon almond, cinnamon spice, creme, creme de menthe, french vanilla, grand mariner, grape, herb blends, Irish creme, kahlua, lemon, macadarain nut, orange, orange leaf, peppermint stick, peach, pistachio, raspberry, sambuca, shawberry and the like, aroma enhancers such as acetaldehyde, caloric or noncaloric sweeteners, dairy components, nondairy components, herbs, spices, as well as mixtures of these components. These other optional components can be added during formation of the soluble coffee products of the present invention or can be included subsequent to the formation of these products.

C. Forming Thermoplastic Coffee Melt Into Elongated Solidified Coffee Structure

The process of the present invention initially involves forming a thermoplastic melt from the soluble coffee solids, water, coffee aroma and flavor volatiles, optionally, but preferably, solubility enhancing components, plus any other optional components that are desired to be incorporated into the soluble coffee matrix. The soluble coffee solids comprise the primary component of the mixture used to form the melt. This mixture comprises from about 85 to about 97%, preferably from about 90 to about 95%, soluble coffee solids. Batch type processes according to the present invention typically have lower levels of coffee solids in this mixture, while continuous type processes (e.g., extrusion) typically have higher levels of coffee solids.

This mixture used to form the melt also comprises from about 3 to about 15% moisture or other source of water. Preferably, the mixture used to form the melt comprises from about 5 to 10% moisture/water. Sources of water can include whatever moisture is present in the coffee aroma and flavor volaries, such as in the case of stripper condensate. When the soluble coffee solids are obtained by concentrating coffee extract to the desired solids content, this concentrated extract can also provide sufficient moisture for the mixture used to form the melt.

The optional solubility enhancing components can be included in mounts effective to enhance the ability of the coffee solids to dissolve in water. When included, the solubility enhancing components typically comprise from about 0.1 to about 5% of the mixture used to form the melt. Preferably, these solubility enhancing components comprise from about 0.1 to about 1% of the mixture. The other optional components, such as noncoffee flavorants, can be included in this mixture in mounts effective to provide the desired benefits. For example, the mixture used to form the melt can comprise up to about 10%, preferably up to about 5%, noncoffee flavorants.

The thermoplastic melt can be formed from this mixture of coffee solids, water, aroma and flavor volatiles, etc., by either batch or continuous processes. Suitable mixers for batch processes include Hobart mixers, kneaders and the like capable of handling highly viscous mixtures. In the case of continuous systems, suitable devices include single and double screw extruders.

In forming the thermoplastic melt from these ingredients, a key aspect of the process of the present invention is to heat the mixture above the glass transition temperature of the coffee solids. By "glass transition temperature" is meant the temperature region where the coffee solids go from a glassy state to a liquefied or melted state. See, for example, U.S. Pat. No. 4,919,962 (Arora et at), issued Apr. 24, 1990, especially column 3, lines 16–35. Heating the mixture to a temperature of at least about 150° F. (65° C.).is usually sufficient to raise the coffee solids above the glass transition temperature. In the process of the present invention, the mixture of coffee solids is typically heated to a temperature of from about 150° to about 210° F. (from about 65.6° to about 99° C.), preferably from about 160° to about 170° F. (from about 71° to about 77° C.), in order to achieve complete melting of the coffee solids. Temperatures in excess of 210° F. (99° C.) can result in the flashing away of important aroma and flavor volatiles and the development of scorched off-flavors in the thermoplastic melt. It is also important that the inclusion of other optional components, such as flavors, does not significantly affect the glass transition temperature of the coffee solids mixture.

The thermoplastic melt can be formed with or without the application of pressure. The particular pressure at which the thermoplastic melt is formed often depends on whether a batch or continuous method is used to form it. For example, when the mixture comprising the coffee solids is extruded (i.e., a continuous method), the mixture is typically subjected to a pressure in the range of from about 15 to about 1000 psig. Forming the thermoplastic melt under pressure is typically used to minimize the loss of aroma and flavor volatiles present in the mixture and to shape the thermoplastic melt across a die of the extruder.

The thermoplastic melt that is formed according to the present invention typically provides a uniform, homogeneous system having a consistency that is anywhere from putty to an extremely viscous flowable mass. Usually, this melt has a consistency similar to that of taffy or other hard candy melts.

The thermoplastic melt of coffee solids is then shaped and solidified to form an elongated coffee structure. This elongated coffee structure can be in the form of a narrow strip but is more typically in the form of a sheet. During the formation of this elongated structure, the temperature of the thermoplastic melt needs to be high enough to allow shaping into the appropriate form (e.g., strip or sheet), yet at the same time be sufficiently low such that melt can eventually solidify to form an outer glassy skin with a molten interior core to avoid sticking to the equipment used to shape it. Typically lowering the temperature of the melt to from about 120° to about 140° F. (from about 48.8° to about 60° C.), i.e., lower than complete melt temperature of the coffee solids, allows it to be shaped into a solidified strip or sheet. Shaping of the thermoplastic melt can be carried out with sheeting rollers, twin roll mills, stamping, or other compresire type devices. Alternatively, the thermoplastic mass can be stretched while in a molten state to provide a thin sheet having a high surface area. It is also highly desirable to remove heat from the thermoplastic mass during the solidification process.

The strip or sheet that is formed is typically an amorphous, noncrystalline, glassy structure. This structure has a thickness of from about 1/16 to about 1/2 inches, preferably from about 1/16 to about 1/4 inches. The aroma and flavor volatiles that are present in the thermoplastic melt become encapsulated within the strip or sheet as it solidifies to form the strip or sheet. If desired, the strip or sheet can be stored for subsequent processing or can be used right away.

D. Controlled Expansion of Solidified Coffee Structure Into porous Coffee Matrix The elongated coffee structure (e.g., strip or sheet) formed from the thermoplastic melt is a relatively dense, nonporous structure. In order to make this structure porous, the strip or sheet is expanded in a controlled manner while in a pliable and deformable state from about 2 to about 10, preferably from about 4 to about 8 times, its initial thickness. This controlled expansion is typically carried out by applying a repeating cycle of vacuum conditions to the strip or sheet while it is heated to gradually puff the structure up without forming large void spaces. For example, quickly applying too high a vacuum (i.e., too low a pressure) can cause the strip or sheet to expand too rapidly and uncontrollably, thus forming large void spaces. The resulting expanded coffee structure having these large void spaces imparts a relatively low compressive strength to the soluble coffee product after granulation.

By "applying a repeating cycle of vacuum conditions" is meant that the vacuum is applied gradually to the strip or sheet over a period of several minutes until the maximum vacuum is reached, with the vacuum then being released (preferably quickly), and then repeating the cycle one or more times until the desired degree of expansion occurs. During a given cycle, the vacuum is gradually applied to the strip or sheet until it reaches a pressure as low as from about 5 to about 50 mmHg before being released. Typically, the vacuum is gradually applied to the strip or sheet until the pressure is as low as from about 5 to about 30 mmHg. Typically, the vacuum is gradually applied over a time period of from about 3 to about 5 minutes. While the vacuum is applied, the strip or sheet is typically heated to a temperature of from about 95° to about 170° F. (from about 35° to about 77° C.), preferably from about 100° to about 150° F. (from about 38° to about 66° C.), so that the strip/sheet is pliable and deformable, and thus capable of expanding. In order to provide the desired controlled expansion, the strip or sheet is typically subjected to vacuum conditions from 2 to 7 times (i.e., the cycle is repeated 1 to 6 times). The conditions under which the strip or sheet is subjected to vacuum conditions can be similar during each cycle or can be different.

The cyclic application of vacuum expands the strip or sheet in a controlled manner such that it forms an amorphous, open-celled, and porous matrix of soluble coffee solids having encapsulated therein the aroma and flavor volatiles. The average pore size can be in the range from about 1 to about 30 microns, but is typically within the range of from about 3 to about 25 microns. The coffee matrix formed typically has a uniform cross sectional pore structure.

Alternatively, the elongated coffee structure can be expanded within the annular space of a porous support structure such as a mold. The mold should have a fixed dimension to control the extent of the vertical expansion of the coffee structure when exposed to vacuum conditions. The use of the annular porous support structure provides additional control over the extent of expansion that can be achieved under a given temperature and vacuum condition. The annular porous support structure can be used in combination with either continuous or cyclic vacuum conditions.

E. Drying and Granulating Expanded Porous Coffee Structure

Once the strip or sheet has been expanded or puffed to form a porous coffee matrix, it is then dried to a moisture content of about 7% or less, preferably from about 3 to about 4%. This porous coffee matrix can be air dried, vacuum dried, microwave dried, dried in a fluidized bed, dried in a vibratory fluidized bed, or the like. This dried matrix is then granulated such as by using a vibratory screen, coffee granulator, low attrition mill, and the like to provide a narrow particle size distribution. (The overs and unders from granulation can be recycled back and used in making thermoplastic coffee melt.) The particle size of this granulated soluble coffee structure is in the range of from about 6 mesh (3360 microns) to about 40 mesh (420 microns). Depending on the particle size distribution, this granulated soluble coffee structure can have a chunkier appearance similar to roast and ground coffee granules or similar to conventional freeze dried coffees. Typically, the granulated soluble coffee structure of the present invention has a Hunter L reading in the range of from about 15 to about 30.

The granulated soluble coffee structure can be further aromatized by the addition of aromatized oil (e.g., aromatized coffee oil). Other optional components such as sweeteners, flavorants, dairy/nondairy solids, etc. can also be added or agglomerated with this granulated soluble coffee structure.

F. Characteristics of Soluble Coffee Product

The soluble coffee products of the present invention have a number of significant characteristics:

(1) The bulk density of the these products is relatively low. Products according to the present invention have bulk densities in the range of from about 0.10 to about 0.35 g/cc, preferably from about 0.15 to about 0.25 g/cc.

(2) Products according to the present invention have a particle density of from about 1.0 to about 1.35 g/cc, preferably from about 1.1 to about 1.2 g/cc.

(3) Products according to the present invention comprise a porous open-celled coffee matrix. These products have a porosity of from about 15 to about 40%, preferably from about 20 to about 30%. Products according to the present invention also have a median pore size of from about 1 to about 30 microns, preferably from about 3 to about 25 microns.

(4) Products according to the present invention exhibit rapid hot water solubility. As a result of their particle densities, porosity and mean pore diameter, the products according to the present invention have sink times of about 45 seconds or less, preferably about 35 seconds or less, most preferably about 10 seconds or less.

(5) Products of the present invention exhibit a higher mechanical strength compared to conventional agglomerated instant coffees, as measured by their compressive strength index. The products according to the present invention have a compressive strength index of about 5 or less, preferably about 3 or less.

EXAMPLES

The following examples illustrate soluble coffee products made according to the present invention.

Example 1

Commercial spray dried soluble powder was alpine milled to 0.5 g/cc bulk density. Four hundred and ninety four grams of this milled powder was placed in a jacketed Hobart mixer heated to 187° F. (86° C.). Six and one quarter grams of aromatized coffee oil was then blended into the milled soluble powder. The resultant coffee powder and oil mixture was heated to 162° F. (72° C.). Fifty grams of ambient temperature distilled water was added over about a 30 second period. A thermoplastic mass formed immediately. This mass was thoroughly mixed for two minutes and then held in the mixer for an additional 11 minutes without agitation. The temperature of the coffee thermoplastic mass was 153° F. (67° C.) prior to sheeting. The coffee melt was compressed into 1/16 to 3/32 inch thick sheets (6–12 inch wide) by multiple passes through a sheeting roll. The sheets were allowed to cool at ambient temperature for about 10 minutes.

These glassy sheets were then subjected to cyclic vacuum conditions to expand their thickness. Seven vacuum cycles were carried out, going from atmospheric pressure to 8 mmHg over a thirty minute period. Each cycle was of about five minutes in duration. The sheet temperature was in the range of from 107°–121° F. (42°–49° C.) as the vacuum was applied. This resulted in controlled expansion of the sheet to a thickness of about ½ inch. The porosity of the sheet was very uniform and visually similar to that of commercial baked bread products.

The expanded sheet was granulated and sized into −8/+12 and −12/+25 mesh sizes and blended at a 50/50 milo. The resulting granulated soluble coffee product had the following physical properties—bulk density of 0.23 g/cc, particle density of 1.1613 g/cc, a moisture content of 6% and a Hunter color of 22.1 (L), 6.2 (a), and 8 (b). The sink time of the product was 15 seconds. The product exhibited very good solubility and yielded a clean cup when added either to a cup of water or dissolved by the addition of water. Expert flavor evaluation of the product at 1% concentration showed good flavor strength and character.

Example 2

Fifty grams of expelled and filtered coffee oil was added to a 250 ml round bottom flask. One half gram of Amano AP6 lipase (61,500 units of activity/gram) was dissolved in 50 grams of distilled water and then added to the coffee oil. The reaction mixture temperature was maintained at 72° F. (22° C.) by a thermowatch and vigorously stirred with a magnetic stirrer for 48 hours. The residual lipase was inactivated by heating the oil to 90° C. and holding for 15 minutes. The oil was allowed to gravity separate from the water and emulsion phase. Carbon number profile (CNP) analysis (see column 17, line 64 to column 19, line 39 of U.S. Pat. No. 5,142,072 (Stipp et al), issued Aug. 25, 1992) showed that the lipase treated oil had 6.1% free fatty acids, 1% monoglyceride, 20.1% diglyceride and 72.8% triglyceride.

Three batches of coffee product were made using the procedure described in Example 1. The solubility effects of the untreated and lipase treated coffee oils are shown in the following table:

| Sulubility Component | Bulk Density (gm/cc) | Sink Time (seconds) | Solubility Evaluations (coffee/water) |
|---|---|---|---|
| None | 0.20 | 45 | Particles floated but dissolved with stirring, foam, slight cup residue |
| 0.5% Coffee Oil | 0.25 | 25 | Particles initially floated but dissolved with stirring, moderate foam, clean cup |
| 0.5% Lipase Hydrolyzed Coffee Oil | 0.20 | <8 | Particles break surface, slight foam (dissipated in about 20 seconds), clean cup |

As can be seen in the above table, the addition of lipase treated coffee oil unexpectedly improved both the rate of particle wetting and the resultant cup appearance. It is believed that the lipase treated coffee oil functions effectively as a surfactant to reduce the surface tension of the water around the coffee particle. This enhances the wetting rate of the particle and in turn the rate of solubility in hot water.

EXAMPLE 3

A series of three runs was made using an extruder to provide shaped and flavor encapsulated coffee products.

A Werner Pfleiderer SZK 30 mm twin-screw extruder was set up with five heads and a ½ inch round hole die. Alpine milled soluble coffee having a bulk density of 0.5 g/cc was volumetrically metered into the first zone of the extruder using a weigh belt system. Coffee oil was preblended into the milled soluble powder in two of the runs: The coffee powders were mixed with either water or stripper condensate. The head temperatures were high enough such that a thermoplastic coffee melt formed within the extruder barrel. The operational conditions of the extruder for the three runs are shown in the following table:

The coffee melt was cooled at ambient for about 10 minutes before the milling/sheeting operation, allowing the skin of the extrudate to solidify to reduce stickiness during the milling/sheeting operation. The extrudate was compressed into ⅛ to 3/32 inch thick strips (6–12 inch wide) by multiple passes through a sheeting roll or single pass through a cooled two roll mill.

The coffee glass sheets were held for one day in sealed plastic bags before drying. The sheets were vacuum dried in two steps. First, the vacuum was applied over five cycles (from atmospheric to 14 mmHg) over a thirty minute period. Each cycle was of about five minute duration. The product temperature was in the range of from 93°–105° F. (34°–41° C.) during the application of the vacuum. This resulted in controlled expansion of the sheet to about ½ to ¾ inch thickness. The expanded sheet was then further vacuum dried for an additional 15 minutes at 5 mmHg at a sheet temperature of 97°–105° F. (36°–41° C.).

The dried sheet was granulated and sized into −8/+12 and −12/+25 mesh sizes and blended at a 50/50 weight ratio. The physical and solubility properties of these products are summarized below:

| Parameter | No Coffee Oil | 1% Coffee Oil/ Stripper Condensate | 1% Coffee Oil/ Stripper Condensate |
|---|---|---|---|
| Batch | 1 | 2 | 3 |
| Coffee Oil Added To Soluble Powder (%) | None | 1 | 1 |
| Liquid Source | Water | Condensate | Condensate |
| Powder Feed (lb/hr) | 15 lb/hr (6.8 kg/hr) | 15 lb/hr (6.8 kg/hr) | 21.5 lb/hr (9.8 kg/hr) |
| Water Feed (lb/hr) | 1.9 lb/hr (0.86 kg/hr) | 1.9 lb/hr (0.86 kg/hr) | 1.9 lb/hr (0.86 kg/hr) |
| Head #1 Temperature | 190° F. (88° C.) | 171° F. (77° C.) | 176° F. (80° C.) |
| Head #2 Temperature | 156° F. (69° C.) | 151° F. (66° C.) | 140° F. (60° C.) |
| Head #3 Temperature | 156° F. (69° C.) | 167° F. (75° C.) | 176° F. (80° C.) |
| Head #4 Temperature | 145° F. (63° C.) | 163° F. (73° C.) | 178° F. (81° C.) |
| Die Temperature | 163° F. (73° C.) | 164° F. (73° C.) | 190° F. (88° C.) |
| Screw Speed (rpm) | 200 | 200 | 200 |
| Torque (%) | 22–25 | 28–38 | 40–47 |

| Property | No Coffee Oil | 1% CoffeeOil/ Stripper Condensate | 1% Coffee Oil/ Stripper Condensate |
| --- | --- | --- | --- |
| Bulk Density (gm/cc) | 0.13 | 0.32 | 0.23 |
| Moisture (%) | 3.3 | 6.8 | 6.2 |
| Color (Hunter L,a,b) | 22.9, 7.4, 8.6 | 17.7, 4.3, 4.4 | 20.3, 5.7, 6.7 |
| Particle Density (gm/cc) | 1.1229 | 1.2801 | 1.1625 |
| Porosity (%) | 39.3 | N/A | 33.5 |
| Mean Pore Diameter - Volume Basis (μ) | 21.4865 | N/A | 3.3048 |
| Compressibility Index | N/A | 2.6 | 4.0 |
| Sink Time (seconds) | 33 | 33 | 22 |
| Solubility (−8/+12 mesh fraction) | heavy foam | slight foam (broke quickly), trace sediment on cup walls | slight foam (broke quickly), trace cup sediment |

The above products were cupped at a 0.75% concentration by expert coffee flavorists and judged to be of good quality. The products containing the added oil and stripper condensate were judged to be more flavorful than the control product.

EXAMPLE 4

Coffee stripper condensate was concentrated using a 4.4 square foot Millipore Prolab reverse osmosis system with a Nonomax-95 membrane. The condensate was processed at 72° F. (22° C.) until the volume was reduced to about 1/10 of the initial feed volume. Chromatographic analysis indicated a 5 fold volatile concentration after membrane processing.

Commercial spray dried soluble powder was alpine milled to 0.5 g/cc bulk density. Four hundred and ninety seven and one-half grams of this powder was placed in a jacketed Hobart mixer and heated to 168° F. (76° C.). Two and one half grams of lipase treated coffee oil (prepared according Example 2 ) was then blended into the milled soluble powder. Fifty grams of chilled membrane processed stripper condensate and distilled water (50/50 ratio) was added over 30 seconds. A thermoplastic mass formed immediately. This mass was thoroughly mixed for four minutes. The coffee mass was then held in the mixer for about an additional 5 minutes without agitation.

The temperature of the thermoplastic coffee mass was 148° F. (64° C.) prior to sheeting. The initial moisture content was 9.78%. The coffee melt was compressed into 1/8 inch thick sheets (6–12 inch wide) by multiple passes through a sheeting roll. The sheets were allowed to cool at ambient temperature for about 5 minutes.

The coffee glass sheets were vacuum dried in two stages. The vacuum was cycled six times from atmospheric to 8 mmHg over a thirty minute period. Each cycle was of about five minutes in duration. The product temperature ranged from 121°–136° F. (49°–58° C.) during this treatment. This resulted in controlled expansion of the sheet to about 1/2 inch thickness. The sheet was dried an additional 10 minutes at 5 mmHg at a temperature of 131° F. (55° C.). The porosity of the dried sheet was very uniform and had snap when broken.

The expanded sheet was granulated and sized to −8/+12 and −12/+25 mesh sizes and blended at a 50/50 ratio. The product had the following physical properties: bulk density of 0.18 g/cc; moisture of 4.6%; Hunter color of 26.4 (L), 6.8 (a), and 10.6 (b). The sink time of the product was 10 seconds. The product solubility was very good and yielded a clean cup when added either to a cup of water or dissolved by the addition of water. Expert flavor evaluation of the product at a 0.75% concentration showed good flavor strength and highly aromatic flavor character. Unexpectedly, the product had a very pleasant nutty flavor and was non bitter that is believed to be due to the lipase treatment removing the bitterness typically seen in soluble products containing high level of coffee oils.

EXAMPLE 5

A Werner Pfleiderer SZK 30 mm twin-screw extruder was set up with five heads and a ½ inch round hole die. Commercial soluble coffee was alpine milled to 0.5 g/cc bulk density, and volumetrically metered into the first zone of the extruder using a weigh belt system. The soluble coffee was mixed with water and heated to form a thermoplastic coffee melt within the extruder barrel. The extruder conditions are shown in the table below:

| Parameter | Condition |
| --- | --- |
| Powder Feed | 25.4 lb./hr (11.5 kg./hr) |
| Water Feed | 1.9 lb./hr (0.86 kg./hr) |
| Head #1 Temperature | 172° F. (78° C.) |
| Head #2 Temperature | 140° F. (60° C.) |
| Head #3 Temperature | 149° F. (65° C.) |
| Head #4 Temperature | 153° F. (67° C.) |
| Die Temperature | 168° F. (76° C.) |
| Screw Speed | 200 rpm |
| Torque | 62% |

The coffee melt was allowed to cool at ambient temperature for about 10 minutes before the sheeting operation. This solidified the skin of the extrudate and reduced stickiness during the subsequent sheeting operation. The extrudate was then compressed into 1/8 to 3/32 inch thick sheets (6–12 inch wide) by multiple passes through a sheeting roll.

The coffee glass sheets were held for ten days in sealed plastic bags before drying. The moisture content of the coffee glass sheets was 6.1%. The sheets were vacuum dried in two steps. First, the vacuum was cycled six times from atmospheric to 10 mmHg over a thirty minute period. Each cycle was of about five minutes in duration. The sheet temperature ranged from 93°–112° F. (34°–44° C.) during this treatment. This resulted in controlled expansion of the sheets to about ½ to ¾ inch thickness. The expanded sheets were vacuum dried for an additional 20 minutes at 5 mmHg at 97° F. (36° C.).

The dried sheets were granulated and sized to −8/+12 and −12/+25 mesh sizes and blended at a 50/50 ratio. The product had the following physical properties: bulk density of 0.14 g/cc; particle density of 1.3198 g/cc; moisture of 4.8%; Hunter color of 25.4 (L), 7.6 (a), and 9.9 (b). The sink time of the product was 15 seconds. The product solubility was good and yielded a clean cup when added either to a cup of water or dissolved by the addition of water.

Example 6

The effect of two different levels of coffee oil (1% and 1.5%) was evaluated using continuous and cyclic vacuum drying treatments.

Commercial spray dried soluble powder was alpine milled to 0.5 g/cc bulk density. Six hundred and ninety three grams was placed in a jacketed Hobart mixer heated to 185° F. (85° C.). Seven grams of coffee oil (1% of the batch) was then blended into the milled soluble powder. The resultant coffee powder and off mixture was heated to 156° F. (69° C.). Seventy grams of ambient temperature distilled water was added over about a 40 second period. A thermoplastic melt formed immediately. This melt was thoroughly mixed for 3 minutes and then held in the mixer for an additional 5 minutes without agitation.

The temperature of the thermoplastic coffee melt was 173° F. (78° C.) prior to sheeting. The coffee melt was compressed into 1/16 to 3/32 inch thick sheets (6–12 inch wide) by multiple passes through a sheeting roll. The strips were allowed to cool at ambient temperature for about two hours in plastic bags. The moisture content of the strips was 7.1%.

A second run was carded out using the same procedure described above except that 10.5 grams of coffee off (1.5% of the batch) was used. The thermoplastic mass was heated to 163° F. (73° C.) prior to sheeting. The sheets were allowed to cool at ambient temperature for about 1½ hours in plastic bags. The moisture content was 7.0%.

The coffee glass sheets from both runs were vacuum dried using both cyclic and continuous conditions. In the first case, the vacuum was cycled five times from atmospheric to 11 mmHg over a 22 minute period. Each cycle was of about four minutes in duration. The sheet temperature ranged from 106°–114° F. (41°–46° C.) during this vacuum treatment. This resulted in controlled expansion of the sheets to about 1/2 inch thickness. The expanded sheets were further dried for about 30 minutes using 5–10 mmHg vacuum at 109° F. (43° C.). In the second case, the coffee glass sheets were dried continuously for about 45 minutes at 5–7 mmHg at 91°–95° F. (33°–35° C.). The vacuum was gradually applied over a 5 minute period.

The sheets were granulated and sized to −8/+12 and −12/+25 mesh sizes and blended at a 50/50 ratio. The physical and solubility properties of these products are shown in the following table:

| Parameter | A | B | C | D |
| --- | --- | --- | --- | --- |
| Oil Level | 1 | 1 | 1.5 | 1.5 |
| Vacuum Treatment | Cyclic | Continuous | Cyclic | Continuous |
| Bulk Density (g/cc) | 0.21 | 0.15 | 0.25 | 0.17 |
| Particle Density (g/cc) | 1.1645 | 1.0671 | 1.1529 | 1.0704 |
| Moisture (%) | 4.5 | 6.6 | 5.4 | 7.2 |
| Sink Time (−8/+12 mesh) | 20 | 25 | 20 | 15 |
| Solubility (coffee to water) | trace sediment | trace sediment | slight foam, clean cup | heavy foam, trace sediment |

These data show that the cyclic application of vacuum increased particle and bulk density. In particular, the cyclic application of vacuum provides products having bulk density in the preferred ranges of 0.15–0.25 g/cc.

EXAMPLE 7

The sheeted and solidified coffee glass of Example 3 (batch 1) was stored in plastic bags 40 days before expansion. The sheet was still pliable and deformable at ambient temperature. The 1/16–1/8 inch thick glass sheet was supported on a solid plate. A 25 mesh screen (707 micron) was held over the coffee glass sheet and spaced vertically from the sheet about 3/8 inches with spacers. The screen was weighted to prevent displacement.

The coffee glass sheet was confined within the 3/8 inch annular porous support structure and heated to 137°–147° F. (58°–64° C.) and held under a 2 mmHg vacuum for 40 minutes. The glass sheet expanded and filled the annular opening of the support structure. The same coffee glass sheet was also expanded, but without confinement in an annular porous support structure. This glass sheet expanded very nonuniformly to about 3/4 inch thickness. Both the confined and unconfined porous coffee structures were cooled to ambient temperature after vacuum expansion.

The unconfined coffee structure had a very nonuniform porosity, was full of very large bubbles, and was very fragile and easily broken. By contrast, the confined coffee structure had a more uniform and smaller cell porosity, and was less fragile and more resistant to breakage.

Similar results were achieved when the coffee glass sheet was expanded in a ½ inch annular porous support structure. The confined glass sheet expanded to ½ inch thickness. The resulting coffee structure had more uniform and controlled porosity than the unconfirmed control sample.

What is claimed is:

1. Soluble coffee products having a particle size in the range of from about 6 mesh (3360 microns) to about 40 mesh (420 microns), which comprise:
   a. a soluble amorphous porous open-celled coffee matrix having:
      (1) a bulk density of from about 0.10 to about 0.35 g/cc;
      (2) a particle density of from about 1.0 to about 1.35 g/cc;
      (3) a porosity of from about 15 to about 40%;
      (4) a median pore size of from about 1 to about 30 microns;
      (5) a sink time of about 45 seconds or less
      (6) a compressive strength index of about 5 or less;
      (7) a moisture content of about 7% or less; and
   b. coffee aroma and flavor volatiles encapsulated within said soluble coffee matrix.

2. The coffee product of claim 1 wherein said bulk density is from about 0.15 to about 0.25 g/cc and wherein said particle density is from about 1.1 to about 1.2 g/cc.

3. The coffee product of claim 2 wherein said porosity is from about 20 to about 30% and wherein said median pore size is from about 3 to about 25 microns.

4. The coffee product of claim 2 wherein said sink time is about 35 seconds or less.

5. The coffee product of claim 4 wherein said sink time is about 10 seconds or less.

6. The coffee product of claim 2 wherein said compressive strength index of about 3 or less.

7. The coffee product of claim 2 wherein said moisture content is from about 3 to about 4%.

8. The coffee product of claim 1 which further comprises an effective amount of a solubility enhancing component.

9. The coffee product of claim 2 wherein said solubility enhancing component comprises from about 0.1 to about 5% of the coffee product and wherein said solubility enhancing component is selected from the group consisting of coffee oil, coffee oil derived fatty acids, water soluble salts of said coffee oil derived fatty acids, monoglycerides and diglycerides of coffee oil derived fatty acids, lipase treated coffee oil, water soluble salts of lipase treated coffee oil, monoglycerides and diglycerides of lipase treated coffee oil, and mixtures thereof.

10. The coffee product of claim 9 which comprises from about 0.1 to about 1% of said solubility enhancing component.

11. Soluble coffee products having a particle size in the range of from about 6 mesh (3360 microns) to about 40 mesh (420 microns), which comprise:

a. a soluble amorphous porous open-celled coffee matrix having:
  (1) a bulk density of from about 0.10 to about 0.35 g/cc;
  (2) a particle density of from about 1.0 to about 1.35 g/cc;
  (3) a median pore size of from about 1 to about 30 microns;
  (4) a sink time of about 45 seconds or less
  (5) a compressive strength index of about 5 or less; and
b. coffee aroma and flavor volatiles encapsulated within said soluble coffee matrix.

\* \* \* \* \*